US008641637B2

(12) United States Patent
Sly et al.

(10) Patent No.: US 8,641,637 B2
(45) Date of Patent: Feb. 4, 2014

(54) METHOD OF MEASURING AN ACOUSTIC IMPEDANCE OF A RESPIRATORY SYSTEM AND DIAGNOSING A RESPIRATORY DISEASE OR DISORDER OR MONITORING TREATMENT OF SAME

(75) Inventors: Peter Sly, East Perth (AU); Zoltan Hantos, Szedged (HU); Cindy Thamrin, South Perth (AU)

(73) Assignee: Telethon Institute for Child Health Research, Subiaco (AU)

( * ) Notice: Subject to any disclaimer, the term of this patent is extended or adjusted under 35 U.S.C. 154(b) by 1366 days.

(21) Appl. No.: 11/921,807

(22) PCT Filed: Jun. 9, 2006

(86) PCT No.: PCT/AU2006/000797
§ 371 (c)(1),
(2), (4) Date: May 29, 2008

(87) PCT Pub. No.: WO2006/130922
PCT Pub. Date: Dec. 14, 2006

(65) Prior Publication Data
US 2009/0062672 A1    Mar. 5, 2009

(30) Foreign Application Priority Data

Jun. 10, 2005    (AU) .............................. 2005903034

(51) Int. Cl.
*A61B 5/05*    (2006.01)
*A61B 5/08*    (2006.01)

(52) U.S. Cl.
USPC ............ 600/529; 600/533; 600/538; 600/547

(58) Field of Classification Search
None
See application file for complete search history.

(56) References Cited

U.S. PATENT DOCUMENTS

| 4,326,416 A | | 4/1982 | Fredberg |
| 5,555,880 A | * | 9/1996 | Winter et al. ............ 128/204.21 |

FOREIGN PATENT DOCUMENTS

| DE | 101 31 823 A1 | 1/2003 |
| WO | WO 93/11703 A1 | 6/1993 |

OTHER PUBLICATIONS

Frey et al "High-frequency respiratory input impedance measurements in infants assessed by the high speed interrupter technique" Eur. Respir. J. 1998, 12: 148-158.*
Stocks et al "Reference values for residual volume, functional residual capacity and total lung capacity" Eur. Respir. J., 1995, 8: 492-506.*
Janssens et al "Physiological changes in respiratory function asociated with ageing" Eur. Respir.J., 1999, 13: 197-205.*

(Continued)

*Primary Examiner* — Betty Forman
(74) *Attorney, Agent, or Firm* — Preti Flaherty Beliveau & Pachios LLP

(57) ABSTRACT

The present invention provides a method of measuring an acoustic impedance of a respiratory system. The method comprises selecting a frequency range for an acoustic wave, directing the acoustic wave into the respiratory system and receiving an acoustic wave from the respiratory system. The method also comprises determining the acoustic impedance for a plurality of volumes or volume ranges of the respiratory system. Each volume, or the volumes within each volume range, is larger than RV or FRC and smaller than TLC whereby the determined acoustic impedances are specific for respective volumes or volume ranges. Further, the method includes determining a volume, or volume range, dependency of the acoustic impedance of the respiratory system and characterizing the respiratory system by analyzing the dependency of the acoustic impedance on the volume or volume range.

11 Claims, 3 Drawing Sheets

(56) References Cited

OTHER PUBLICATIONS

Loos et al. "Respiratory and upper airways impedance responses to methacholine inhalation in spontaneously breathing cats" Eur. Respir. J. 2000, 15: 1001-1008.*

Louis et al., "*Dual Assessment of Airway Area Profile and Respiratory Input Impedence From a Single Transient Wave*," Journal of Applied Physiology 90:2001, pp. 630-637.

Kong et al., "*Measurement of Respiratory Acoustic Impedance in Children by a Modified Forced Oscillation Method*," Proceedings of the 20th Annual International Conference of the IEEE Engineering in Medicine and Biology Society, vol. 20, No. 6, 1998, pp. 3223-3225.

Lutchen et al., "*Use of Transfer Impedance Measurements for Clinical Assessment of Lung Mechanics*," American Journal of Respiratory and Critical Care Medicine, vol. 157, pp. 435-446, 1998.

Harper et al., "*An Acoustic Model of the Respiratory Tract*," IEEE Transactions on Biomedical Engineering, vol. 48, No. 5, May 2001, pp. 543-550.

Lutchen et al., "*Relationship Between Heterogeneous Changes in Airway Morphometry and Lung Resistance and Elastance*," Journal of Applied Physiology 83(4): 1192-1201, 1997.

Van Den Elshout, F.J., "Variations of respiratory impedance with lung volume in bronchial hyperreactivity," Chest, Official publication off the American College of chest Physicians, vol. 98, No. 2, Aug. 1, 1990, pp. 358-364.

Oostveen, E. et al., "The forced oscillation technique in clinical practice: methodology, recommendations and future developments," European Respiratory Journal, vol. 22, 2003, pp. 1026-1041.

Briscoe, William A. et al., "The Relationship Between Airway Resistance, Airway Conductance and Lung Volume In Subjects of Different Age and Body Size," J. Clin. Invest, vol. 37, No. 9, Sep. 1958, pp. 1279-1285.

Marchal, F. et al., "Methacholine-induced volume dependence of respiratory resistance in preschool children," The European Respiratory Journal, vol. 14, No. 5, Nov. 1999, pp. 1167-1174.

Birch, Malcolm et al., "An analogue instrument for the measurement of respiratory impedance using the forced oscillation technique," Physiological Measurement, vol. 22, No. 2, May 2001, pp. 323-339.

Pohlmann, Andreas et al., "Effect of changes in lung volume on acoustic transmission through the human respiratory system," Physiological Measurement, vol. 22, No. 1, Feb. 2001, pp. 233-243.

\* cited by examiner

US 8,641,637 B2

METHOD OF MEASURING AN ACOUSTIC IMPEDANCE OF A RESPIRATORY SYSTEM AND DIAGNOSING A RESPIRATORY DISEASE OR DISORDER OR MONITORING TREATMENT OF SAME

This application is a §371 national phase filing of PCT/AU2006/000797 filed Jun. 9, 2006, and claims priority to Australian application No. 2005 903034 filed Jun. 10, 2005.

FIELD OF THE INVENTION

The present invention broadly relates to a method of measuring an acoustic impedance of a respiratory system.

BACKGROUND OF THE INVENTION

Respiratory diseases including cystic fibrosis, asthma, chronic obstructive pulmonary disease, bronchitis, and other respiratory diseases characterised by an inflammatory response are particular difficult diseases to diagnose early and/or monitor during therapy.

The acoustic impedance of a human respiratory system is often measured to obtain information concerning resistive and elastic properties of airways and tissues. Emphysema, for example, affects the elastic properties of the airways and tissues and it is possible to diagnose emphysema from results of the acoustic impedance measurements.

Acoustic impedance measurements of the human respiratory system are usually conducted using a forced oscillation technique in which acoustic waves are directed into the respiratory system and a response is detected. Frequencies that are selected for the acoustic waves are relatively low, such as a few Hertz, as for such low frequencies mathematical models are available that facilitate analysis of the measurement data. A patient breathes during the acoustic impedance measurements and the obtained data are characteristic for one or more breathing cycles.

Such measurements are useful as they provide valuable information about the respiratory system. For a more comprehensive diagnose, however, additional information is required and there is a need for technological advancement.

SUMMARY OF THE INVENTION

The present invention provides in a first aspect a method of measuring an acoustic impedance of a respiratory system, the method comprising:
  selecting a frequency range for an acoustic wave,
  directing the acoustic wave into the respiratory system,
  receiving an acoustic wave from the respiratory system,
  determining the acoustic impedance for a plurality of volumes or volume ranges of the respiratory system, each volume, or the volumes within each volume range, being larger than RV or FRC and smaller than TLC whereby the determined acoustic impedances are specific for respective volumes or volume ranges,
  determining a volume, or volume range, dependency of the acoustic impedance of the respiratory system and
  characterising the respiratory system by analysing the dependency of the acoustic impedance on the volume or volume range.

Throughout this specification the abbreviations FRC, RV, TLC are used for functional residual capacity, residual volume and total lung capacity, respectively.

The volume ranges may be successive volume ranges and may correspond to tidal changes in volume.

For example, it is possible to characterise, from the analysis of the volume or volume range dependency of the acoustic impedance, if and how the elasticity and/or resistivity of the airways and tissues of the respiratory system depend on the volume of the respiratory system.

The acoustic impedance typically is determined at or near resonance or anti-resonance condition at which the acoustic impedance typically has a minimum and maximum respectively.

The respiratory system typically is a human respiratory system.

The frequency of the acoustic wave typically is selected so that the acoustic impedance of the respiratory system is predominantly determined by a predetermined internal region of the human respiratory system. The selected frequency may be as low as a few Hz, but typically is greater than 40, 60, 80, 100 or 200 Hz. At the relatively high frequencies the impedance measurements probe predominantly the airways of the respiratory system, but not of the periphery of the lungs, i.e. the tissues and chest wall.

The acoustic wave typically is directed into the respiratory system and received from the respiratory system during a volume change of the respiratory system from the first volume to the second volume.

The step of selecting a frequency for an acoustic wave typically comprises selecting a plurality of component frequencies of an acoustic signal and the step of directing the acoustic wave into the respiratory system typically comprises directing the acoustic signal into the respiratory system. For example, the acoustic signal may comprise component frequencies within the range of a few Hz to a few hundred Hz.

The step of receiving an acoustic wave from the respiratory system typically comprises receiving an acoustic signal from the respiratory system which is associated with a respective acoustic signal that was directed into the respiratory system.

The step of determining the acoustic impedance typically comprises determining the acoustic impedance from analysis of the acoustic signals that were directed into and received from the respiratory system.

In a second aspect the invention provides method of diagnosing a respiratory disease or disorder in a subject comprising:
  selecting a frequency range for an acoustic wave,
  directing the acoustic wave into the respiratory system of the subject,
  receiving an acoustic wave from the respiratory system,
  determining the acoustic impedance for a plurality of volumes or volume ranges of the respiratory system, each volume, or the volumes within each range, being larger than RV or FRC and smaller than TLC whereby the determined acoustic impedances are specific for respective volumes or volume ranges,
  determining a volume, or volume range, dependency of the acoustic impedance of the respiratory system and
  comparing the acoustic impedance to a reference acoustic impedance obtained from a subject not having the respiratory disease or disorder.

In a third aspect, the invention provides a method of monitoring the progress of therapy targeted at a respiratory disease or disorder in a subject comprising:
  a) selecting a frequency range for an acoustic wave,
  b) directing the acoustic wave into the respiratory system of the subject,
  c) receiving an acoustic wave from the respiratory system,
  d) determining the acoustic impedance for a plurality of volumes or volume ranges of the respiratory system, each volume, or the volumes within each range, being larger than RV or FRC and smaller than TLC whereby the determined acoustic impedances are specific for respective volumes or volume ranges, e) determining a volume, or volume range, dependency of the acoustic impedance of the respiratory system, f) administering therapy to the subject, g) reassessing the subject using method steps a) to e), wherein a change in acoustic impedance during or following therapy monitors the progression of the therapy.

In a fourth aspect of the present invention provides a method for determining the potential responsiveness of a subject to particular forms of therapy for a respiratory disease or disorder comprising:

a) selecting a frequency range for an acoustic wave, b) directing the acoustic wave into the respiratory system of the subject, c) receiving an acoustic wave from the respiratory system, d) determining the acoustic impedance for a plurality of volumes or volume ranges of the respiratory system, each volume, or the volumes within each range, being larger than RV or FRC and smaller than TLC whereby the determined acoustic impedances are specific for respective volumes or volume ranges, e) determining a volume, or volume range, dependency of the acoustic impedance of the respiratory system and f) comparing the acoustic impedance to a reference acoustic-impedance obtained from a subject not having the respiratory disease or disorder which thereby predicts the potential responsiveness of the subject to a particular form of therapy.

The change in impedance typically is a decrease relative to acoustic impedance before therapy.

In a fifth aspect the present invention provides a method for predicting the risk of progression to severe and/or persistent respiratory disease or disorder in a subject, comprising:

a) selecting a frequency range for an acoustic wave, b) directing the acoustic wave into the respiratory system of a subject, c) receiving an acoustic wave from the respiratory system, d) determining the acoustic impedance for a plurality of volumes or volume ranges of the respiratory system, each volume, or the volumes within each range, being larger than RV or FRC and smaller than TLC whereby the determined acoustic impedances are specific for respective volumes or volume ranges, e) determining a volume, or volume range, dependency of the acoustic impedance of the respiratory system and f) comparing the acoustic impedance to a reference acoustic impedance obtained from a subject not having the respiratory disease or disorder, wherein a level of impedance greater than the reference is associated with increased risk of progression to severe and/or persistent respiratory disease or disorder.

The frequency of the acoustic wave in the method according to any one of the second to the fifth aspect of the present invention typically is selected so that the acoustic impedance can be determined at or near resonance or anti-resonance.

The method according to any one of the second to the fifth aspects typically comprises determining the acoustic impedance for a plurality of volumes of the respiratory system, each volume being larger than RV or FRC and smaller than TLC whereby the determined acoustic impedances are specific for respective volumes. Alternatively, the method may comprise determining the acoustic impedance for a plurality of volume ranges of the respiratory system, the volumes within each volume range being larger than RV or FRC and smaller than TLC whereby the determined acoustic impedances are specific for respective volume ranges.

DETAILED DESCRIPTION OF THE INVENTION

Figure 1:
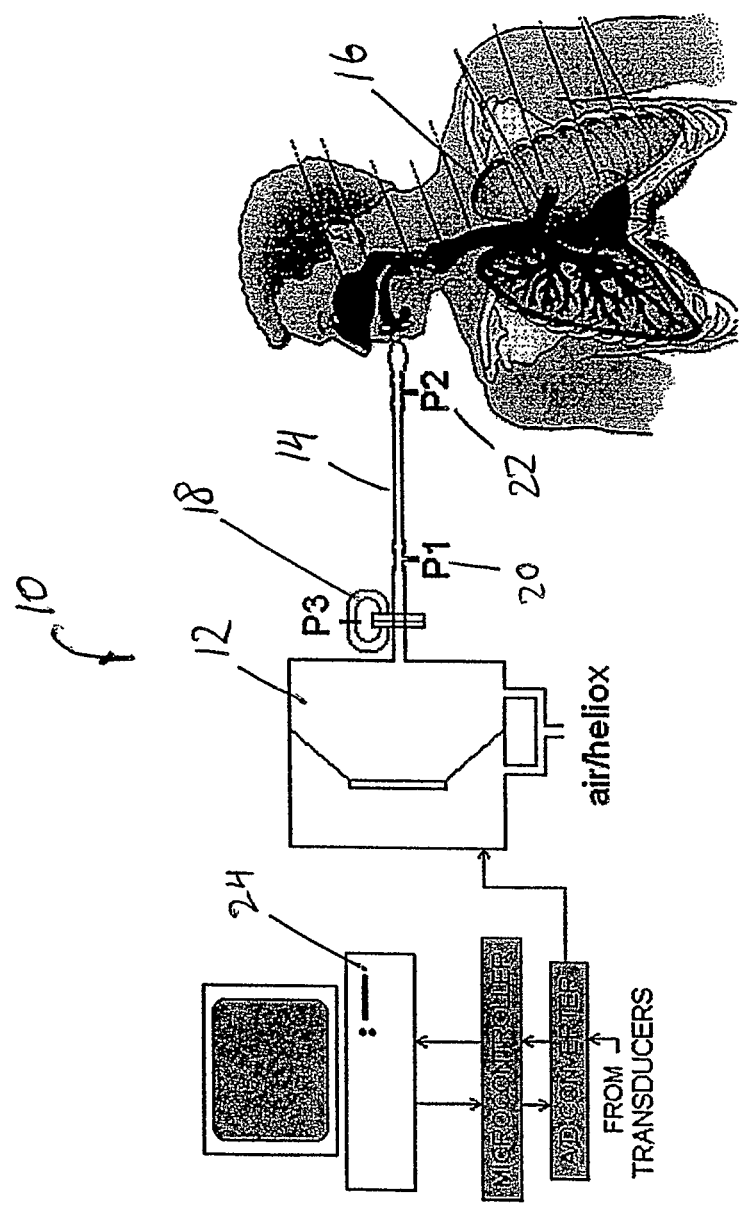
FIG. 1 shows a schematic representation of a measurement set-up for measuring the acoustic impedance of a human respiratory system according to an embodiment of the present invention, FIGS. 2 (*a*) and (*b*) show representative plots of the real component (Rrs) of the acoustic impedance as a function of volume and as a function of frequency.

Before the present methods are described, it is understood that this invention is not limited to the particular materials and methods described, as these may vary. It is also to be understood that the terminology used herein is for the purpose of describing particular embodiments only, and is not intended to limit the scope of the present invention which will be limited only by the appended claims. It must be noted that as used herein and in the appended claims, the singular forms "a," "an," and "the" include plural reference unless the context clearly dictates otherwise. Thus, for example, a reference to "a disorder" includes a plurality of such disorders, and a reference to "an acoustic wave" is a reference to one or more acoustic waves, and so forth. Unless defined otherwise, all technical and scientific terms used herein have the same meanings as commonly understood by one of ordinary skill in the art to which this invention belongs. Although any materials and methods similar or equivalent to those described herein can be used to practice or test the present invention, typical materials and methods are now described.

All publications mentioned herein are cited for the purpose of describing and disclosing the protocols, reagents and devices which are reported in the publications and which might be used in connection with the invention. Nothing herein is to be construed as an admission that the invention is not entitled to antedate such disclosure by virtue of prior invention.

The present invention relates to methods of diagnosing "respiratory diseases or disorders" or methods of monitoring the effectiveness of treatment of respiratory diseases or disorders. Examples of respiratory diseases or disorders that can be diagnosed or monitored by the methods and devices of the present invention include cystic fibrosis, asthma, emphysema, chronic obstructive pulmonary disease, bronchitis, and other respiratory diseases characterised by an inflammatory response.

The term "subject" as used herein refers to any vertebrate species which can suffer from a respiratory disease or disorder. The methods of the present invention are particularly useful in the diagnosis of respiratory diseases or disorders in warm-blooded vertebrates. Thus, in a specific embodiment, the invention concerns mammals and birds.

In one specific embodiment the present invention is concerned primarily with the diagnosis of respiratory diseases or disorders in human subjects of any age, but can also be employed for the diagnosis of other mammalian subjects, such as dogs, cat, livestock, primates and horses, for veterinary purposes.

As used herein, the terms "diagnosis" or "diagnosing" refers to the method of distinguishing a subject with a respiratory disease or disorder from a subject not having a respiratory disease or disorder, wherein the subject not having the respiratory disease or disorder is considered "normal". The subject may have the early symptoms of a respiratory disease or disorder or maybe asymptomatic.

The present invention also relates to a method for predicting the development of a respiratory disease or disorder. The term "predicting the development" when used with reference to a respiratory disease or disorder means that the subject does not have a respiratory disease or disorder or does not have clinical symptoms of a respiratory disease or disorder, but they have a propensity to develop a respiratory disease or disorder.

In one embodiment, the term "predicting the development" also includes subjects that have a respiratory disease or disorder and the methods disclosed herein are used to more accurately determine the severity of the disease or disorder or predict its progression.

Referring now to FIG. 1, a method of measuring an acoustic impedance of a respiratory system according to an embodiment of the present invention is now described.

In this embodiment a forced oscillation technique (FOT) is used for the acoustic impedance measurements using measurement set-up 10. An acoustic signal is generated by signal generator 12 and directed via wavetube 14 into human respiratory system 16. The acoustic signal is formed by a number of acoustic waves having respective frequencies. In this example a majority of the frequencies that are associated with the acoustic signal are selected so that the acoustic impedance can be measured at anti-resonance. The acoustic impedance at higher frequencies, such as 40 Hz or higher, probes predominantly the airways but not the periphery of the lungs, i.e. the tissues and chest wall. The majority of the frequencies were also selected so that they are sufficiently high to predominantly probe the airways. In this example the acoustic signal was formed by 39 waves having respective frequencies ranging from 5 to 302.5 Hz.

In this example the wavetube 14 had an internal diameter of 12.7 mm and a length of 245 mm. Transducers 20 and 22 were used to measure the acoustic impedance at ends of the wavetube 14 and a pneumo-tachometer 18 was used to determine the air flow. Lung volume was estimated by integrating air flow detected by the pneumo-tachometer 18. The acoustic impedance was determined using computer system 24 which also controlled the acoustic signal generator 12 and received data from the pneumo-tachometer 18 and the transducers 20 and 22. A suitable software routine was used to control the measurements, determine the impedances and display data.

During the measurements subjects made various breathing manoeuvres over periods of 20 seconds. During the breathing manoeuvres a number of the acoustic impedance measurements were undertaken each within a period of time which is short compared with the time required for a breathing cycle. The software routine is in this example arranged to determine the acoustic impedance during each short time interval while the lung volume of a subject is changing. For example, the successive volume ranges for which the acoustic impedance is measured may correspond to tidal changes in volume. The software determines an average acoustic impedance value for each short period of volume change, such as a volume change during a period of 0.4 seconds, rather than an average acoustic impedance value representative for an entire breathing cycle. Consequently each measured acoustic impedance is characteristic for a specific volume range.

When the measurements commenced, subjects were either instructed to begin with an inspiration from FRC to TLC followed by an expiration to RV, or to begin with an expiration from FRC to RV followed by an inspiration to TLC. For subjects having emphysema the measurement protocol was simplified to tidal breathing followed by an inspiration from FRC to TLC.

The acoustic impedance was determined for 16 healthy adult subjects and for 12 adult subjects having emphysema. General characteristics and lung function parameters of the two groups are summarised in Table I.

TABLE I

|  | Healthy subjects | Subjects with Emphysema |
| --- | --- | --- |
| Gender | 8 males, 8 females | 10 males, 2 females |
| Age (median, range) | 41 yrs, 24-69 yrs | 68 yrs, 51-78 yrs |
| Height (median, range) | 171 cm, 151-183 cm | 166 cm, 156-177 cm |
| Weight (median, range) | 73.7 kg, 45.0-103.4 kg | 69.3 kg, 51.0-84.8 kg |
| FEV1 % predicted (mean, SD) | 98.98 ± 7.95% | 51.40 ± 22.51% |
| TLC % predicted (mean, SD) | 96.92 ± 11.97% | 125.13 ± 8.34% |
| DLCO (mean, SD) | N/A | 45.67 ± 16.54% |
| DLCO, corrected for Valv (mean, SD) | N/A | 56.18 ± 15.29% |

Table I. General characteristics and lung function parameters for the healthy subjects and subjects with emphysema. The abbreviation "FEV1" is used for a volume of air exhaled in the first second during a standard forced expiratory manoeuvre from total lung capacity. The abbreviation "DLCO" is used for the diffusing capacity for carbon monoxide. DLCO is used to determine an efficiency of gas transport between alveolar air and blood in the pulmonary circulation (as the DLCO is corrected for Valv, the DLCO is normalized between subjects by correcting for the amount of air (ie gas volume) in the alveoli).

Figure 2:
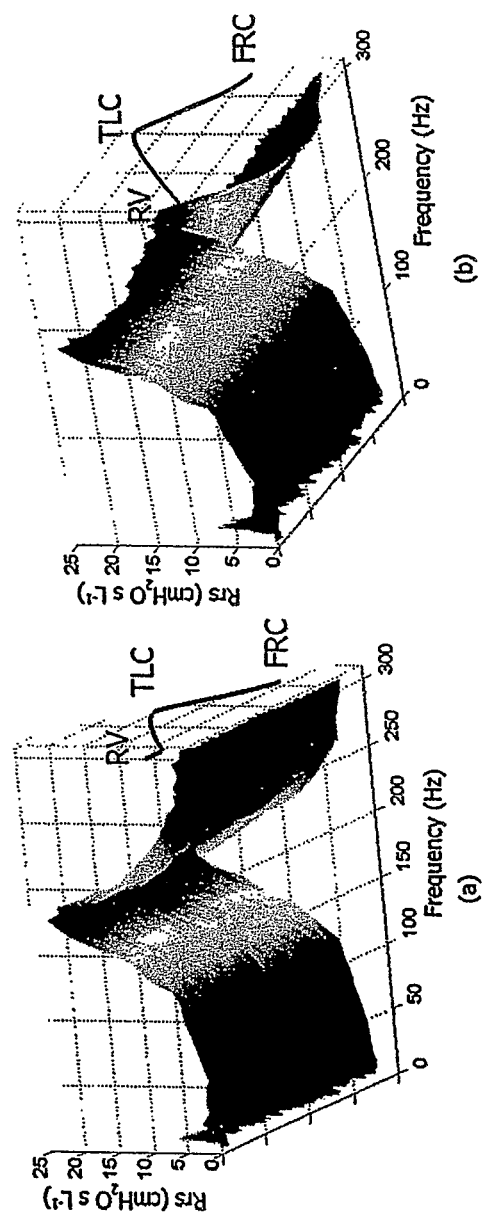

FIGS. 2 (a) and (b) show representative plots of the real component Rrs of the acoustic impedance for a healthy subject as a function of frequency and as a function of volume which changes from FRC to TLC and to RV. For each volume the plots shown in FIG. 2 (a) have a maximum at a particular frequency. The maximum indicates anti-resonance (far,1) and the plots show how the frequency at which anti-resonance occurs changes when the volume changes. FIG. 2 (b) shows the same plot from a slightly different perspective to visualise the dependency of the magnitude of Rrs on the volume of the respiratory system. The plots show that far,1 decreases as the volume changes from FRC to TLC, and then increased as volume decreases to RV.

For all healthy subjects an inspiratory limb of Rrs for a volume change from FRC and TLC was found to be relatively free of artefacts, compared to data obtained at lung volumes below FRC or during expiration. Consequently data analysis focused on the dependency of Rrs on the volume between FRC and TLC.

The results indicate that the relationship between anti-resonance parameters and volume is linear.

Figure 3:
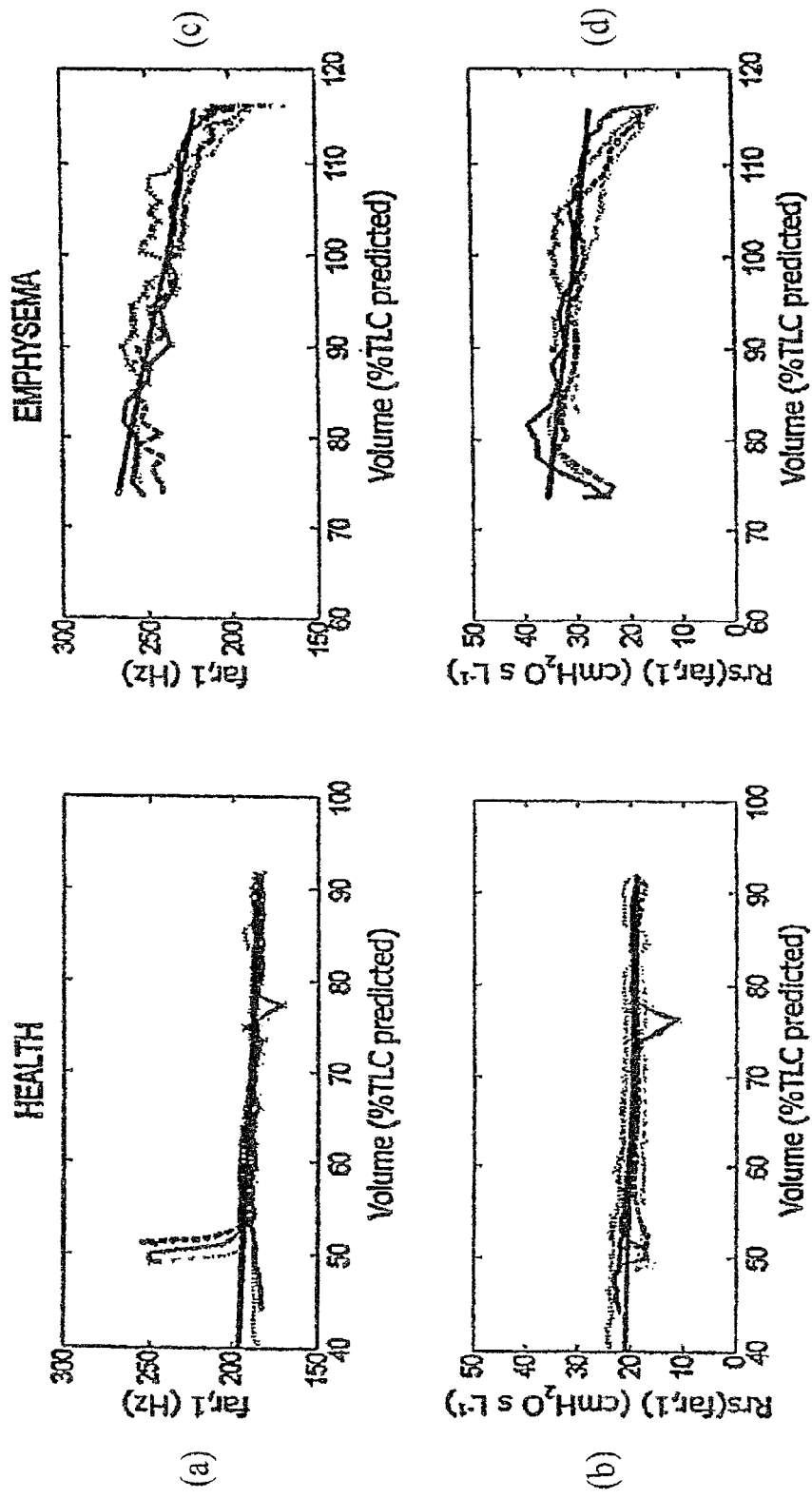
FIG. 3 shows plots of the anti-resonance frequency as a function of volume ((a) and (c)) and the real component (Rrs) of the acoustic impedance at anti-resonance frequency as a function of volume ((b) and (d)).

FIG. 3 shows plots for (a) far,1 for healthy subjects as a function of volume, (b) Rrs (far,1) for healthy subjects as a function of volume, (c) far,1 as a function of volume for subjects with emphysema and (d) Rrs (far,1) as a function of volume for subjects with emphysema. These plots show the linear dependency of far,1 and Rrs on the volume and also show linear fits which were derived from average slops and intercepts of all measurements that were conducted.

The data for subjects having emphysema were found to have steeper negative slopes compared with the data for healthy subjects (for both far,1 and for Rrs(far,1)). A study of the relationship between the slopes of plots for far,1 and Rrs (far,1) as a function of volume indicated a mild but significant correlation for far,1 ($r=-0.439$), and a stronger relationship for Rrs(far,1) ($r=-0.589$) with a degree of hyperinflation.

As indicated above, the acoustic impedance at higher frequencies, such as frequencies of 40 Hz or higher, probes predominantly the airways but not the periphery of the lungs, i.e. the tissues and chest wall. Considering a simple model of a network of parallel resonant compliant tubes for an airway tree associated with the human respiratory system, the decrease in far,1 with increasing volume (see FIG. 2) is consistent with an expected increased mean path length for wave propagation within the airway tree as the lung expands. Median values for far,1 correspond to an effective path length of 40.6 cm at static FRC and 44.8 cm at TLC, assuming a tube of equivalent length (using speed of sound in free air $c=340$ m/s). This indicates an increased path length of 4.2 cm from FRC to TLC. However, treating each possible path for wave propagation as an acoustic transmission line, the behaviour of far,1 may alternatively be explained in terms of an increased effective compliance in the airways. As the lungs expand, a greater gas compressibility with the increase in bulk gas volume is expected in distended airways, while airway walls become less compliant with distension. Only the former would contribute to the observed shift in far,1 to lower frequencies.

Although the invention has been described with reference to particular examples, it will be appreciated by those skilled in the art that the invention may be embodied in many other forms. For example, the acoustic impedance may not be measured while the volume of the respiratory system is changing. In a variation of the described embodiments the volume may not change for a small period of time during which a volume specific acoustic impedance may be measured. In this manner a range of volume specific acoustic impedance measurements may be conducted each of which being specific for a different particular volume of the respiratory system. Further, it is to be appreciated that the acoustic impedance measurements may not necessarily be conducted at anti-resonance conditions, but may alternatively be conducted at resonance conditions or at any other suitable condition. In addition, the respiratory system may not necessarily be human.

The invention claimed is:

1. A method of measuring an acoustic impedance of a respiratory system, the method comprising:
    selecting a frequency range for an acoustic wave,
    directing the acoustic wave into the respiratory system,
    receiving an acoustic wave from the respiratory system and determining the acoustic impedance for a plurality of successive volume ranges of the respiratory system, each volume range corresponding to a tidal change in volume and each volume within each volume range being larger than FRC and smaller than TLC, comprising determining an average of the acoustic impedance for each volume range whereby the determined acoustic impedances are specific for respective volume ranges,
    determining a linear volume range dependency of the acoustic impedance of the respiratory system for said plurality of successive volume ranges, and
    characterizing the respiratory system by analysing the slope of the linear dependency of the acoustic impedance on the volume range,
    wherein the acoustic impedance is determined at or near resonance or anti-resonance condition.

2. The method as claimed in claim 1 wherein the frequency of the acoustic wave is selected so that the acoustic impedance of the respiratory system is predominantly determined by a predetermined internal region of the human respiratory system.

3. The method as claimed in claim 2 wherein the predetermined internal region comprises the airways, but not the periphery of the lungs.

4. The method as claimed in claim 1 wherein the selected frequency range has a lower limit that is greater than 40 Hz.

5. The method as claimed in claim 1 wherein the selected frequency range has a lower limit that is greater than 60 Hz.

6. The method as claimed in claim 1 wherein the selected frequency range has a lower limit that is greater than 100 Hz.

7. The method as claimed in claim 1 wherein the acoustic wave is directed into the respiratory system and received by the respiratory system during a volume change of the respiratory system.

8. The method as claimed in claim 1, further comprising:
    receiving the acoustic wave from the respiratory system and determining the acoustic impedance for a plurality of volumes of the respiratory system, each volume being larger than FRC and smaller than TLC whereby the determined acoustic impedances are specific for respective volumes,
    determining a linear volume dependency of the acoustic impedance of the respiratory system for said plurality of volumes, and
    characterizing the respiratory system by analyzing the slope of the linear dependency of the acoustic impedance on the volume.

9. The method as claimed in claim 8, wherein the frequency of the acoustic wave is selected so that the acoustic impedance of the respiratory system is predominantly determined by a predetermined internal region of the human respiratory system; the predetermined internal region comprises the airways, but not the periphery of the lungs; and wherein the selected frequency range has a lower limit that is greater than 40 Hz.

10. The method as claimed in claim 8, wherein the acoustic wave is directed into the respiratory system and received from the respiratory system during a volume change of the respiratory system.

11. The method as claimed in claim 8, further comprising determining the acoustic impedance for a plurality of volumes of the respiratory system, each volume being larger than FRC and smaller than TLC.

* * * * *